US006440105B1

(12) United States Patent
Menne

(10) Patent No.: US 6,440,105 B1
(45) Date of Patent: Aug. 27, 2002

(54) EJECTION DEVICE FOR THE HIGH-PRESSURE EJECTION OF A LIQUID

(75) Inventor: Andreas Menne, Meersburg (DE)

(73) Assignee: Ferton Holding SA, Delemont (CH)

( * ) Notice: Subject to any disclaimer, the term of this patent is extended or adjusted under 35 U.S.C. 154(b) by 0 days.

(21) Appl. No.: 09/467,920

(22) Filed: Dec. 21, 1999

(30) Foreign Application Priority Data

Dec. 21, 1998 (DE) .......................................... 198 59 133

(51) Int. Cl.[7] ............................................. A61M 5/315
(52) U.S. Cl. .......................... 604/218; 604/70; 604/131
(58) Field of Search ..................... 604/68–72, 131–133, 604/140–147, 187, 218, 228–233

(56) References Cited

U.S. PATENT DOCUMENTS

| 5,697,917 A | * 12/1997 | Sadowski et al. ............ 604/218 |
| 5,704,911 A | * 1/1998 | Parsons ........................ 604/72 |

FOREIGN PATENT DOCUMENTS

| DE | 295 07 987 | 10/1996 |
| DE | 19618971 A1 | 11/1997 |
| EP | 0 317 507 | 4/1992 |
| EP | 0 771 219 | 2/1999 |

* cited by examiner

Primary Examiner—Glenn K. Dawson
Assistant Examiner—Jennifer Maynard
(74) Attorney, Agent, or Firm—Griffin & Szipl, P.C.

(57) ABSTRACT

An ejection device for ejecting a liquid or a liquid containing solid particles at high pressure, comprising a head unit; a pressure chamber (11) which opens into a distal ejection opening and is delimited by a working piston which, upon application of an elastic impact on its end facing away from the pressure chamber, is capable of transmitting a compression wave which may displace the pressure chamber-facing end of the working piston into the pressure chamber so that the volume thereof is reduced, with the reduction in volume of the pressure chamber being significantly smaller than the original volume of the pressure chamber; and a drive unit having a drive member which is accelerated across an acceleration portion formed within the drive unit so that it generates the elastic impact to be transmitted to the working piston. The pressure chamber is at least partially formed by a pressure cavity formed in the head unit. The need unit and the drive unit are formed as separate, independent units which are mounted to each other by a separable mounting coupling. An intermediary member is provided between the working piston and the acceleration portion as a separate component to transmit the elastic impact from the drive member to the working piston, said intermediary member being arranged in the drive unit of the device. Further, the acceleration portion of the drive unit is tightly sealed by the intermediary member.

10 Claims, 3 Drawing Sheets

EJECTION DEVICE FOR THE HIGH-PRESSURE EJECTION OF A LIQUID

Figure 1:
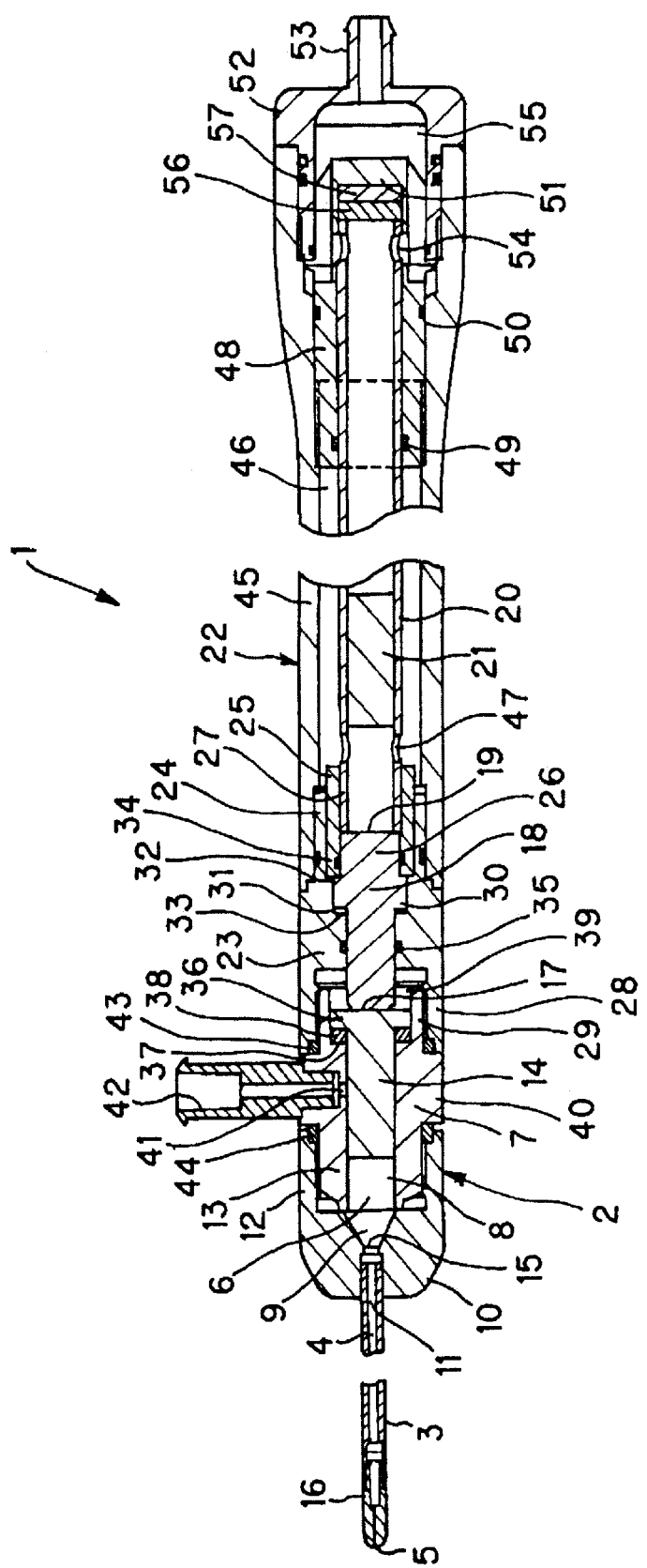

This application claims priority of German Patent Application Number 198 59 133.0-41, filed Dec. 21, 1998, the entire disclosure of which is considered to be part of the present disclosure and is specifically incorporated by reference herein.

The present invention relates to an ejection device for the high-pressure ejection of a liquid or a liquid containing solid particles, comprising a head unit and a pressure chamber which opens into a distal ejection opening and is delimited by a working piston which, upon application of an elastic impact on its end facing away from the pressure chamber, is capable of transmitting a compression wave by which the pressure chamber-facing end of the working piston is displaceable into the pressure chamber so that the volume thereof is reduced. The reduction in volume of the pressure chamber is significantly smaller than the volume of the pressure chamber resulting in high-pressure ejection of a small quantity of the liquid through the ejection opening. Further, the ejection device comprises a drive unit having a drive member which is accelerated along an acceleration portion within the drive unit to generate the elastic impact to be transmitted to the working piston.

Ejection devices of the above described type are known, for example, from EP 771 219, which describes said devices as being specially designed for the ejection of precisely dosed, minute amounts of liquid, which may be in the range of cubic millimeters, so that these devices are particularly well-suited as medical instruments for the injection of minute doses of liquid drugs which are to be administered with high precision.

The ejection of such small amounts of liquid is achieved by the drive member transmitting only an elastic impact to the working piston so that the latter is not moved any further into the pressure chamber by the drive member. That is, after having transmitted the impact, the drive member no longer exerts any external driving force upon the working piston so that the amount of liquid contained in the pressure chamber and defined by the working piston is not ejected in the way it would in a common syringe, but exclusively by means of the compression wave excited by the impact transmitted through the working piston. The compression wave propagates into the pressure chamber and causes the liquid to be ejected from the ejection opening at high pressure. The ejection pressure, and thus the volume or amount of liquid ejected from the opening, may be precisely controlled by suitably adjusting the velocity of the drive member since this velocity determines the magnitude of the impact which is transmitted.

According to the ejection devices described in EP 0 771 219, the volume of the pressure chamber considerably exceeds the stroke volume of the working piston so that a small, precisely dosed amount of liquid may be ejected regardless of the actual size of the pressure chamber.

To prevent the drive member from exerting any external force on the working piston after the impact has been transmitted, it is possible, for example, to stop the application of a driving force acting on the drive member towards the working piston as soon as the transmission of the impact starts, or to provide a stopper which prevents the drive member from transmitting any force to the working piston after the impact has been transmitted.

The working piston is preferably made of a solid material which transmits elastic shock waves with as little loss as possible, such as a metallic material. The drive member may be any component which can be accelerated across an acceleration portion, such as a drive piston which may be accelerated within a drive pipe and is preferably coaxially aligned with the working piston. However, the drive member may also be designed other than as a piston, for example as a plate or a rocker arm which acts upon the working piston so that a driving impact is exerted thereupon.

The drive member may be driven pneumatically, hydraulically, mechanically, or electromagnetically. The means driving the drive member may be designed such that they enable only a single working stroke of the drive member. However, the drive member may preferably be driven such that it successively transmits periodically repeated impact pulses so that the total amount of liquid being ejected may be controlled by suitably adjusting the number of repetitions.

In the endoscopic version known from EP 0 771 219, the working piston is formed as a probe extending within the endoscopic catheter and having a proximal probe head arranged in an acceleration pipe. The acceleration pipe accommodates a working piston which acts upon the probe head so that a compression wave is excited within the probe that causes the end of the probe located in the catheter to be displaced into the pressure chamber formed by the lumen of the catheter, so that liquid is ejected.

However, the ejection devices known from EP 0 771 219 are difficult to clean and sterilize because of the integral structure of their head units containing the liquid to be ejected.

The present invention provides an ejection device of the initially mentioned type whose head unit may be easily cleaned and sterilized, and which at the same time enables an adequate protection of the liquid to be ejected from contamination, and in particular from any contamination caused by the drive unit of the device.

According to the present invention, the pressure chamber of the ejection device is at least partially formed by a pressure cavity provided in the head unit of the device. Furthermore, the head unit and the drive unit of the device are formed as separate, independent units which are mounted to each other by means of a separable mounting coupling. Further, an intermediary member is provided between the working piston and the acceleration portion, which is formed as a separate component and transmits the elastic impact from the drive member to the working piston. Said intermediary member is arranged in the drive unit of the device and provides a tight seal between the acceleration portion of the drive unit and the working piston.

Since the head unit and the drive unit of the ejection device according to the present invention are designed as separate units which are separably connected to each other, the head unit containing the liquid to be ejected may be easily and separately cleaned and sterilized. The drive unit requires either no sterilization at all, or only local sterilization at its end facing the head unit. Since said two units of the ejection device are separately sealed, and since especially the acceleration portion of the drive unit is sealed against the head unit, any contamination of the liquid accommodated in the head unit by dirt particles or pathogens present in the drive unit is safely prevented. Further, it is possible to easily and, thus, quickly replace the head unit by another one containing a different liquid drug, for example.

In the ejection device according to the present invention, the impact is transmitted via the intermediary member which is acted upon by the drive member. When the drive member abuts against the intermediary member, a shock wave is excited within the intermediary member which propagates therethrough and is transmitted by the intermediary member to the working piston which in turn transmits the shock wave into the liquid contained in the pressure chamber. The intermediary member is particularly advantageous since it transmits the impact to the working member while remaining itself in a stationary position, provided that it has been designed with a suitable mass and abuts against the working piston preferably without play. In this way, the sealing of the acceleration portion achieved by means of the intermediary member is ensured also during impact transmission.

This sealing principle for impact drives is also described in DE 196 18 971 A1, although in connection with a kidney stone crusher.

The intermediary member is preferably made of a solid material which transmits elastic shock waves possibly without loss, such as a metallic material. Further, the intermediary member is preferably formed as a piston-shaped body, and its axial motion is limited by stoppers in both directions, with a small axial play being allowed between the intermediary member and the stopper which is proximate to the working piston so that any pulse transmission from the intermediary member to the stopper proximate to the working piston is prevented, which ensures a loss-free transmission of impact pulses to the working piston.

According to a preferred embodiment, the head unit comprises a sleeve-type insert which accommodates the working piston and is mounted to the drive unit by means of the separable mounting coupling. A cap is separably mounted to the insert and comprises a pressure cavity outlet that forms the fluid connection with the ejection opening. The pressure cavity may be formed exclusively in the insert, for example by designing the hollow provided in the insert to accommodate the working piston with a greater length. However, the pressure cavity may also be formed by a cavity as described above which combines with an adjacent recess formed in the cap.

This two-part structure of the head unit enables it to be disassembled for cleaning and sterilization so that it is more readily accessible for cleaning tools. The connection between the insert and the cap may be formed, for example, by a plug-in connection, a bayonet fastener or a screw-type connection.

Although the propagation of the compression wave and, thus, any leakage of liquid from the pressure chamber may be prevented by minimizing the gap between the cap and the insert, it is preferable to provide an elastic seal which seals the gap between cap and insert so that the liquid is more safely protected from contamination by pathogens, for example. Further, it is also preferable to provide an elastic seal sealing the gap between the insert and the drive unit of the device so that pathogens are effectively prevented from invading between these two parts as well.

To enable a periodic operation of the ejection device according to the present invention, a liquid filling neck is provided which is advantageously formed at the insert and communicates with the pressure cavity via the gap between the working piston and the insert. The gap between the working piston and the insert is large enough to provide a sufficient fluid connection between the pressure chamber and the liquid filing neck, and narrow enough to ensure that the propagation of compression waves excited in the pressure chamber through the gap and rearwardly towards the liquid filling neck is minimized. Further, it is thus not necessary to provide a separate supply passage which would require additional sterilization or had to be provided with a check valve. The liquid filling neck may, for example, be designed as a neck which is inserted or threaded into the side surface of the insert. For this purpose, the insert preferably comprises a radial flange which is formed in the longitudinal center thereof and serves both as a base for the liquid filling neck and as a handle which facilitates the mounting of the insert including the cap to the drive unit. Alternatively, the liquid filling neck may be provided at the cap which in this case comprises a passage formed therein that is controlled by a check valve and connects the pressure chamber to the filling neck.

To improve the efficiency of the ejection device, the working piston is sealed against the insert by means of an elastic sealing element which is arranged around the circumference of the piston at a position behind the liquid filling neck, as seen from the pressure chamber. Said sealing element prevents the leakage of liquid into the drive unit so that the liquid may exit the pressure chamber only through the ejection opening. Furthermore, the sealing element prevents the compression wave from propagating through the gap between the working piston and the insert so that, secondarily, a rearward ejection of liquid from the pressure chamber is prevented.

The elastic sealing element may be arranged, for example, in an inner annular groove formed in the insert so that it sealingly abuts against the circumference of the working piston. However, according to a preferable embodiment, the end of the working piston which is distal to the pressure chamber is provided with a radial flange so that the elastic sealing element may be arranged between said flange and a shoulder formed in the insert, at the side of the flange facing the pressure chamber. This design is advantageous because during ejection the elastic sealing element will thus be pressed on by an increased pressure, because the impact transmitted to the piston pushes the piston and its flange towards the shoulder formed in the insert. Thus, the sealing of the pressure chamber is further improved. Further, the sealing element advantageously ensures that the working piston always returns to its original axial position, i.e. the position it had before the impact, which is preferably a position where it abuts against the intermediary member so that the intermediary member is pressed against the stopper distal to the working piston, which ensures that an axial play is maintained between the intermediary member and the stopper proximal to the working piston. Said play is necessary for a trouble-free operation of the device. To enable the discharge of fluid also at times when the device is not operating, the sealing element is advantageously arranged to be elastically biased between the flange and the shoulder formed in the insert. The returning of the working piston together with the intermediary member to their respective original positions may also be ensured by the sealing element arranged in the annular groove formed in the insert as mentioned above, if said sealing element is elastically biased in said groove so that any axial displacement of the working piston relative to the sealing element is prevented.

Preferably, a compensation cavity is provided around the gap between the working piston and the intermediary member and filled with gas such as air, for example. In the case of the working piston being separated from the intermediary member during impact transmission, the space formed between them will create a negative pressure which may interfere with the motion of the working piston. However, since the compensation cavity is larger than the space created between the intermediary member and the piston, this pressure drop is so small that it does not affect the motion of the working piston.

According to an embodiment, the ejection device according to the present invention is formed as an endoscopic ejection device. For this purpose, the head unit of the device is connected to an endoscopic catheter comprising a lumen, which enables the passage of liquid therethrough, and the ejection opening, with the pressure chamber being formed by the lumen of the catheter and by the pressure cavity formed between the lumen and the working piston.

With the embodiment, the formation of at least part of the pressure chamber within the head unit has the advantage that any residues produced by abrasive wear during the motion of the working piston will mainly be found in the head unit rather than within the lumen of the catheter. Thus, there is a decreased risk of particles resulting from abrasion being ejected, and the removal of such particles is easier because the head unit may be designed in such a way as to be more easily accessible by cleaning devices than the elongated, narrow catheter specially designed for insertion. In general, any movable components such as another check valve preventing air from being sucked back into the pressure chamber, for example, may be arranged within the head portion so that the endoscopic catheter only serves as a passage for the liquid and may thus be formed with particularly small dimensions. The head unit may also be connected to different catheters of any desired inner diameter without difficulty, and with the endoscopic device remaining fully functional.

The catheter may be fastened to the head unit, and preferably to the end thereof which is opposite the working piston, by means of a screw-type or plug-in connection, for example. Correspondingly, in the case of a multiple-part version of the head unit comprising the cap, the catheter will advantageously be mounted to the cap. The endoscopic catheter may be formed as a rigid or as a flexible catheter. Furthermore, it may be designed for insertion into the operating passage of an endoscope. For endoscopic applications, the ejection device and the endoscope may preferably be combined to form one single unit.

In view of the prefered use of the device according to the invention, the walls surrounding the pressure chamber and, thus, its surrounding parts such as the insert, cap, working piston and seals should be made of a material which is particularly easy to sterilize any may be kept sterile without difficulty, i.e. they should be made of a very smooth material such as polished steel or titanium or their alloys, for example, which does of course not apply to the seals. Moreover, the materials should be inert with respect to the liquid to be ejected.

To enable the cleaning and sterilization of the device, the mounting coupling may be separated or disconnected so that the head unit may be removed from the drive unit. Next, the working piston may be removed from the insert together with its surrounding sealing element, after which the sealing element may be stripped from the working piston. Further, it is possible to disconnect the cap and the catheter fastened thereto, or the insert and the cap.

To prevent the drive member from accidentally leaving its starting position, a fixing device is provided to fix the drive member at its starting position. The fixing device may be a clamping device, for example, which fixes the drive member by means of clamping forces which may be overcome by the driving forces. Advantageously, a magnetic fixing device is provided for fixing the drive member and formed, for example, by an electromagnet, but preferably by a permanent magnet. The drive member may have magnetic part attached thereto such as a magnetizable metallic member which acts in combination with the magnetic fixing device. Preferably, the entire drive member is made of a magnetizable material such as steel, for example.

Figure 2:
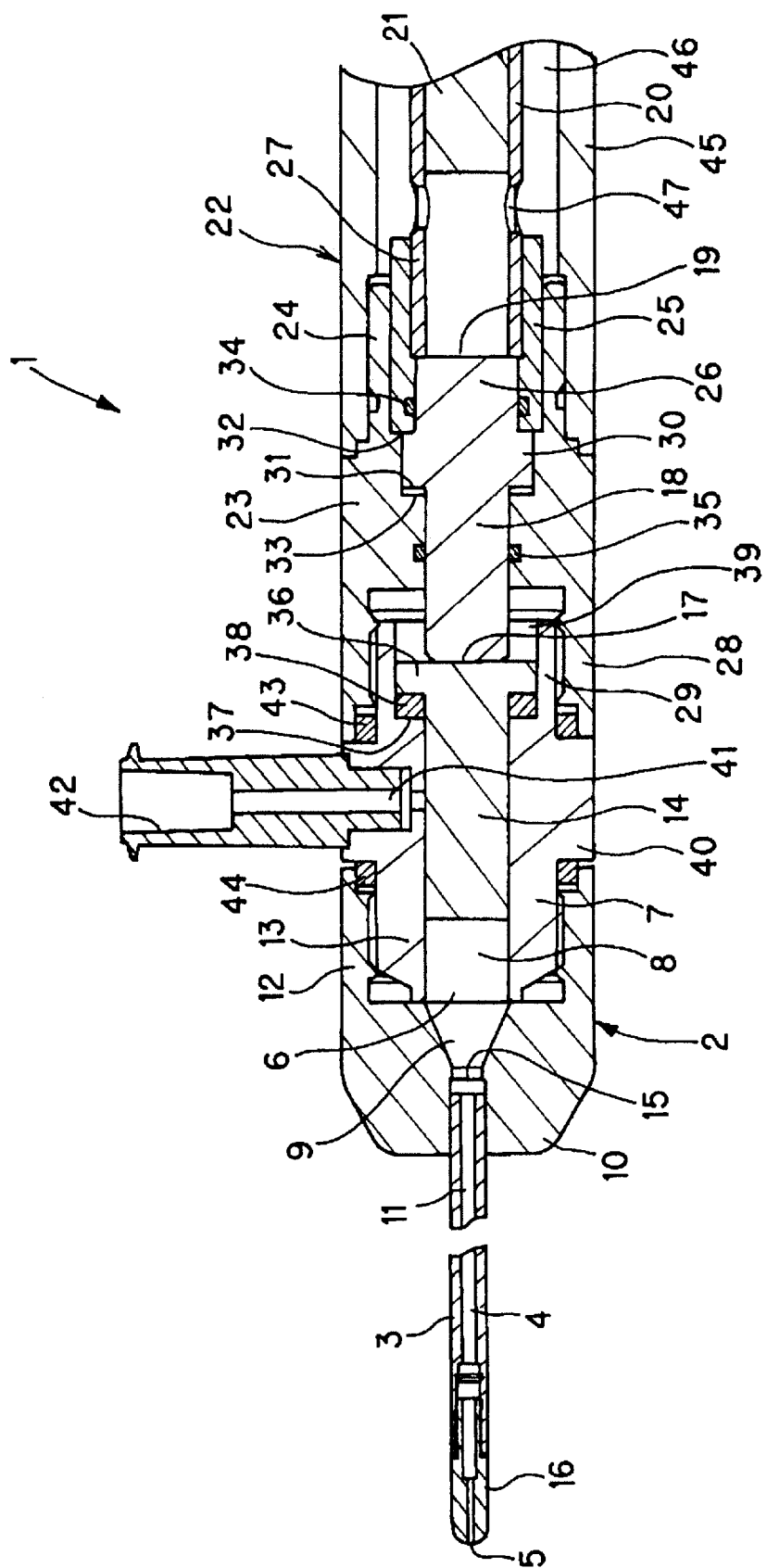

The present invention will now be explained in more detail by means of preferred embodiments thereof and with reference to the accompanying drawing, wherein FIG. 1 shows a longitudinal section of an ejection device according to an embodiment of the present invention, and FIG. 2 shows an enlarged view of the front portion of the ejection device according to FIG. 1.

Figure 3:
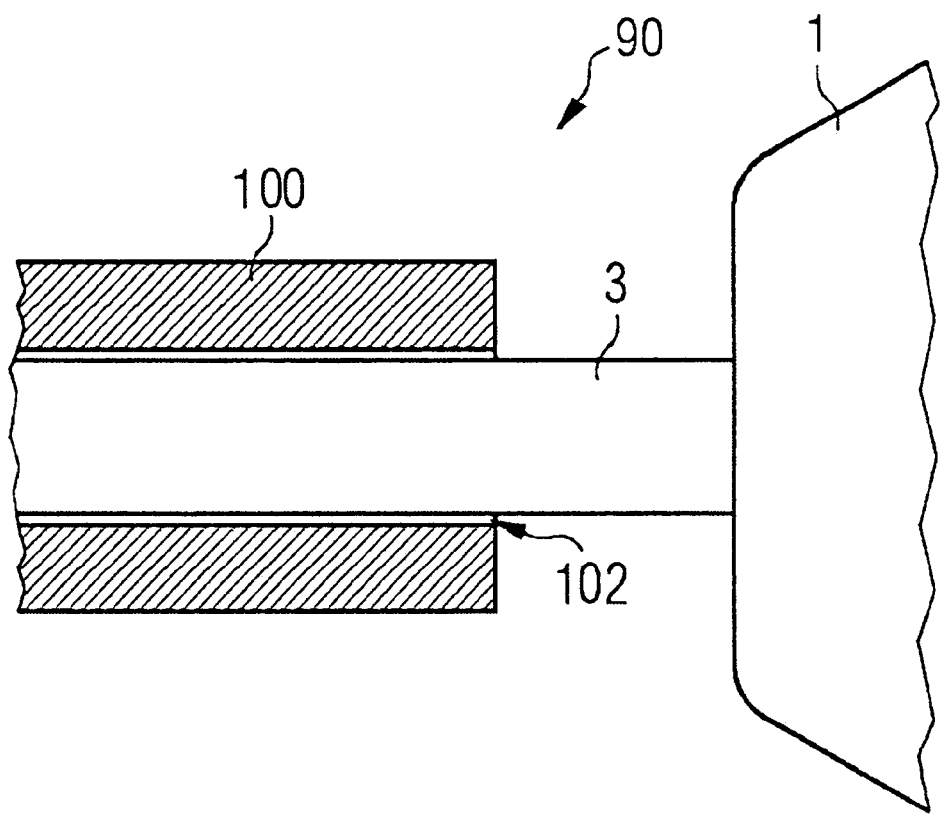

FIG. 3 shows a partial cut away view of one preferred embodiment of the present invention.

FIGS. 1 and 2 each show a longitudinal section of an endoscopic version of an ejection device 1 according to the present invention which may be used for ejecting liquid at high pressure. The ejection device 1 comprises a head unit 2 which is connected to an endoscopic catheter 3 formed by a flexible tube and comprising a lumen 4 formed by a passage as well as an ejection opening 5. The head unit 2 comprises a pressure cavity 6 which consists of a cylindrical hollow 8 formed by a sleeve-type insert 7, as well as of an adjacent recess 9 formed in a cap 10 that is axially threaded upon the insert 7. The recess 9 and the hollow 8 are aligned so that their adjacent edges are flush with each other. Both the insert 7 and the cap 10 are part of the head unit 2. The pressure cavity 6 and the lumen 4 form a pressure chamber 11 wherein the liquid is received.

The cap 10 comprises an axially extending internal thread at its end portion 12 facing the insert 7, which acts in combination with an axial external thread formed at the cap-facing end portion 13 of the insert 7. On its side facing the insert, the pressure cavity 6, and thus also the pressure chamber 11, are delimited by a cylindrical working piston 14 disposed in the hollow 8 of the insert 7. On its side facing the cap, the pressure cavity 6 opens into a pressure cavity outlet 15. For this purpose, the recess 9 in the cap 10 is conically tapered towards the axial direction facing away from the pressure cavity 6. The pressure cavity outlet 15 is connected with the endoscopic catheter 3 whose lumen 4 communicates with the pressure cavity 6 via the pressure cavity outlet 15. For this purpose, the catheter 3 is inserted or threaded into the cap 10 at the face side thereof. Further, the ejection end of the endoscopic catheter 3 comprises an ejection nozzle 16.

At its end face 17 facing away from the pressure cavity 6, the working piston 14 abuts against the end face of an intermediary member 18 which is substantially formed as a cylindrical intermediary piston and arranged coaxially with the working piston 14. At its axial side facing away from the working piston 14, the intermediary member 18 is connected with a cylindrical drive pipe 20 whose end face abuts against the end face 19 of the intermediary member 18 and which is arranged coaxially with the intermediary member 18 and the working piston 14. In the drive pipe 20, a drive member formed by a cylindrical drive piston 21 is disposed to be freely movable in the longitudinal direction of the drive pipe 20. As will be explained in more detail later, the drive piston 21 may be accelerated towards the working piston 14 so that it transmits an elastic impact to the working piston 14 via the interposed intermediary member 18, which impact causes the end of the working piston 14 facing towards the pressure chamber to be displaced into the pressure chamber 11.

The drive piston 21, drive pipe 20 and intermediary member 18 are components of the drive unit 22 to which the head unit 2 is separably mounted, as will be described afterwards.

The drive unit 22 comprises a receiving sleeve 23 which is arranged coaxially with the insert 7 and accommodates the intermediary member 18. At its end portion 24 facing away from the insert 7, the receiving sleeve 23 is inserted with a stuffing box 25 wherein the end portion 26 facing away from the working piston 14 of the intermediary member 18 and the end portion 27 facing towards the working piston 14 of the drive pipe 20 are received. The stuffing box 25 is tightly pressed against the receiving sleeve 23, or, alternatively, sealed against the latter by means of a sealing device. The receiving sleeve 23 comprises an internal thread at its end portion 28 facing the insert 7, and the insert 7 has an external thread at its end portion 29 facing the receiving sleeve 23 and is threaded into the receiving sleeve 23. In the described embodiment, the separable connection between the drive unit 22 and the head unit 2 is formed by the screw-type connection between the insert 7 and the receiving sleeve 23.

The intermediary member 18 comprises a radial flange 30 which is received in a recess 31 so that it has little axial play and no radial play. The axial end surfaces of the recess 31 are formed by an inner edge portion of the end face 32 facing the intermediary member 18 of the stuffing box 25, and by an inner shoulder 33 formed in the receiving sleeve 23. The radial or circumferential surface of the recess 31 is formed by a portion of the cylindrical inner wall of the receiving sleeve 23. The intermediary member 18 is sealed against the stuffing box 25 and the receiving sleeve 23 by O-rings 34 and 35, respectively, which are arranged in front of and behind its annular flange 30, respectively, as seen in the impacting direction of the drive piston 21.

The working piston 14 comprises a radial flange 36 formed at its end facing the intermediary member 18, with an O-ring 38 being disposed between said flange 36 and an inner shoulder 37 formed in the insert, at the flange side facing away from the intermediary member 18. Said O-ring 38 both seals the working piston 14 against the insert 7 and axially biases it against the intermediary member 18 so that the end face of the flange 30 of the intermediary member 18 is pressed against the adjacent end face 32 of the stuffing box 25. An annular chamber 39 is formed around the gap between the working piston 14 and the intermediary member 18, and is defined by the end face of the flange 36 facing the intermediary member 18 and an inner end face facing the working piston 14 of the receiving sleeve 23. The annular chamber 39 is filled with gas and forms a compensation cavity surrounding the intermediary member 18.

The insert 7 comprises an outwardly extending flange 40 which is formed between the two external threads. The flange 40 is provided with a radially extending through hole 41 into which a neck 42 is threaded that serves as a liquid filling neck. The through hole 41 communicates with the pressure cavity 6 and, thus, with the pressure chamber 11 via the gap formed between the working piston 14 and the insert 7 so that the pressure chamber 11 may be supplied with liquid via the neck 42. Two O-rings 43, 44 are abutted against the flange 40 of the insert 7 at both sides thereof. The O-ring 43 seals the circumferential surface of the insert 7 against the receiving sleeve 23, and the O-ring 44 disposed on the other side of the flange 40 seals the circumferential surface of the insert 7 against the cap 10.

The end portion 24 of the receiving sleeve 23 facing away from the insert 7 is provided with a casing that is placed around its circumference and formed by a cylindrical receiving pipe 45 accommodating the drive pipe 20 and being tightly pressed against the receiving sleeve 23. An annular chamber 46 is formed between the receiving pipe 45 and the drive pipe 20 and communicates with the interior of the drive pipe 20 via openings 47 formed laterally in the drive pipe 20 and next to the stuffing box 25.

At its end facing away from the head unit 2, the annular chamber 46 is axially delimited by a sealing sleeve 48 which surrounds the drive pipe 20 and is axially threaded into the receiving pipe 45. O-rings 49, 50 seal the sealing sleeve 48 against the drive pipe 20 and the receiving pipe 45.

The end of the drive pipe 20 facing away from the head unit 2 is tightly closed by a cover 51. The end of the receiving pipe 45 facing away from the head unit 2 is tightly closed by a plug 52 which is formed with a connecting piece 53 for the supply of compressed air. The device pipe 20 is provided with lateral openings 54 located adjacent to the cover 51 which communicate with the opening in the connecting piece 53 via a chamber 55 formed between the plug 52, the sealing sleeve 48, the receiving pipe 45 and the drive pipe 20. A rigid plate 56 and an elastic plate 57 are arranged within the cover 51 and act together as a buffered stop for the drive piston 21. For this purpose, the two plates 56, 57 are arranged in direct contact with each other, with the rigid plate 56 being closer to the drive piston 21. The elastic plate 57 is made of an elastic plastic material or of rubber and serves as a buffer element. The rigid plate 56 is made of a permanent-magnetic material, i.e. it forms a permanent magnet. The drive piston 21 is made of a magnetizable material such as steel. The rigid plate 56 thus forms a magnetic fixing device for the drive piston 21 at which the drive piston 21 is held in its starting position so that it is fixed against accidental movement. The magnetic forces created between the rigid plate 56 and the drive piston 21 are dimensioned such that they may be overcome by the driving forces.

Next, the operation of the above described endoscopic ejection device 1 will be explained. Via the connecting piece 53, the ejection device 1 is supplied with compressed air delivered by a pump (not shown). Via the chamber 55 and the openings 54, the compressed air enters the interior of the drive pipe 20 where it acts upon the drive piston 21 so that the latter is accelerated towards the intermediary member 18. The air which is displaced from the drive pipe 20 by the drive piston 21 is forced through the openings 47 and into the annular chamber 46. The drive piston 21 is only accelerated, i.e. moved by a force created by the supplied compressed air, until it abuts against the intermediary member 18. Then, the air compressed in the annular chamber 46 flows back through the openings 47 and into the drive pipe 20 so that the piston 21 is forced back to its original position.

When the drive piston 21 abuts against the intermediary member 18, it excites an elastic impact on the intermediary member 18 causing a compression wave which propagates through the intermediary member 18 and is transmitted in turn as an elastic impact to the working piston 14, the impact in turn propagating in the working piston 14 as an elastic compression wave. The axial play between the flange 30 of the intermediary member 18 and the inner shoulder 33 of the receiving sleeve 23 prevents the impact from being transmitted from the intermediary member 18 to the receiving sleeve 23. The axial play is ensured by the O-ring 38 arranged behind the flange 36 of the working piston 14, which presses the working piston 14 against the intermediary member 18 whose flange 30 is in turn pressed against the stuffing box 25 so that the axial play necessary for operation is maintained.

The compression wave transmitted to the working piston 14 as described above propagates through the piston 14 and causes its end facing the pressure cavity 6 and, thus, the pressure chamber 11 to be displaced into the pressure chamber 11. As a result, the pressure in the pressure chamber 11 increases so that the liquid contained therein is being ejected out through the ejection opening 5.

The head unit 2 may have a check valve arranged therein which prevents air from being sucked into the lumen 4 through the ejection opening 5. Said check valve may be provided in the cap 10, for example, in the form of a valve controlling the pressure cavity outlet 15. The neck 42 may also be provided with a check valve which only opens to the pressure chamber 11 for the supply of liquid from a reservoir.

The O-ring 38 arranged between the flange 36 and the inner shoulder 37 has another advantage: during impact transmission from the intermediary member 18 to the working piston 14, the O-ring 38 is compressed so that when the pressure increases in the pressure chamber 11, the sealing of the working piston 14 against the insert 7 is improved.

In the case of the working piston 14 separating from the intermediary member 18, the annular chamber 39 surrounding the intermediary member 18 provides for a pressure compensation so that the creation of a negative pressure, which could hinder the displacement of the working piston 14 and, thus, interfere with a troublefree operation of the ejection device, is prevented.

The two-part design of the endoscopic ejection device 1 according to the present invention comprising a head unit 2 and a drive unit 22 has the advantage that the head unit 2 comprising the components for liquid supply and accommodation may be prepared and sterilized separately, i.e. independently from the drive unit 22. Further, if one of the two units 2, 22 becomes defective, only the defective unit rather than the entire device 1 needs to be replaced.

Since the drive unit 22 and the head unit 2 are designed as separate and encapsulated, i.e. sealed, units of the device, the liquid contained in the head unit 2 is more effectively protected from contamination.

In another preferred embodiment of the present invention, endoscopic catheter (3) may be formed as a rigid or as a flexible catheter. Furthermore, endoscopic catheter (3) may be designed for insertion into the operating passage (102) of an endoscope (100). For endoscopic applications, the ejection device (1) and the endoscope (100) may be combined to form one single unit (90) as shown in FIG. 3.

What is claimed is:

1. An ejection device for high-pressure ejection of a liquid or a liquid containing solid particles, comprising:

a head unit;

a pressure chamber which opens into a distal ejection opening and is delimited by a working piston which, upon application of an elastic impact on an end of the working piston facing away from the pressure chamber, is capable of transmitting a compression wave by which a pressure chamber-facing end of the working piston is displaceable into the pressure chamber so that the volume thereof is reduced, with the reduction in volume of the pressure chamber being significantly smaller than the volume of the pressure chamber; and a drive unit having a drive member, the drive member which is accelerated along an acceleration portion within the drive unit to generate an elastic impact to be transmitted to the working piston, characterized in that the pressure chamber is at least partially formed by a pressure cavity provided in the head unit, that the head unit and the drive unit are formed as separate, independent units which are mounted to each other by a separable mounting coupling, that an intermediary member is provided between the working piston and the acceleration portion as a separate component to transmit the elastic impact from the drive member to the working piston, the intermediary member being arranged in the drive unit of the device, and that the acceleration portion of the drive unit is tightly sealed towards the working piston by the intermediary member.

2. An ejection device according to claim 1, characterized in that the head unit comprises a sleeve-type insert which accommodates the working piston and is mounted to the drive unit by means of the separable mounting coupling, with a cap being separably mounted to the insert, said cap comprising a pressure cavity outlet that provides a fluid connection with the ejection opening.

3. An ejection device according to claim 2, characterized in that the insert is sealed against the cap and the drive unit respectively by means of an elastic seal.

4. An ejection device according to claim 2, characterized in that the insert is formed with a liquid filling neck which communicates with the pressure cavity via a gap formed between the working piston and the insert.

5. An ejection device according to claim 2, characterized in that the working piston is sealed against the insert by means of an elastic sealing element.

6. An ejection device according to claim 5, characterized in that the working piston comprises a radial flange at the end facing away from the pressure chamber, with the elastic sealing element being arranged between said flange and a shoulder formed at the insert.

7. An ejection device according to claim 1, characterized in that a compensation cavity is provided around a gap between the working piston and the intermediary member.

8. An ejection device according to claim 1, characterized in that the head unit is connected to an endoscopic catheter which comprises a lumen enabling the passage of liquid therethrough as well as the ejection opening, and that the pressure chamber is formed by the lumen of the catheter and by the pressure cavity.

9. An ejection device according to any one of claims 1 to 8, characterized by an endoscope to which the ejection device is connected to form a single unit.

10. An ejection device according to claim 1, characterized in that the drive member is held in a starting position by a magnetic fixing device.

* * * * *